United States Patent [19]

Hachmann et al.

[11] Patent Number: 4,746,451

[45] Date of Patent: May 24, 1988

[54] SELF-DECONTAMINATING CLEANSING PREPARATIONS

[75] Inventors: Klaus Hachmann, Hilden; Karlheinz Disch, Haan; Klaus Bansemir, Langenfeld, all of Fed. Rep. of Germany

[73] Assignee: Henkel Kommanditgesellschaft auf Aktien, Duesseldorf, Fed. Rep. of Germany

[21] Appl. No.: 892,023

[22] Filed: Jul. 30, 1986

[30] Foreign Application Priority Data

Aug. 10, 1985 [DE] Fed. Rep. of Germany ....... 3528843

[51] Int. Cl.[4] ......................... A61K 7/50; C11D 3/39; C11D 3/48; C11D 17/08

[52] U.S. Cl. .................................. 252/102; 252/89.1; 252/106; 252/174.19; 252/541; 252/545; 252/546; 252/548; 252/551; 252/DIG. 5; 424/130

[58] Field of Search .................. 424/130; 252/95, 102, 252/106, 548, DIG. 5, 551, 544, 546, 545

[56] References Cited

U.S. PATENT DOCUMENTS

| | | | |
|---|---|---|---|
| 3,440,319 | 4/1969 | Wilson | 252/95 |
| 4,321,156 | 3/1982 | Bushman | 252/142 |
| 4,329,334 | 5/1982 | Su | 424/70 |
| 4,387,040 | 6/1983 | Straw | 252/368 |
| 4,491,539 | 1/1985 | Hoskins | 252/541 |
| 4,557,898 | 12/1985 | Greene | 424/130 |

FOREIGN PATENT DOCUMENTS

| | | | |
|---|---|---|---|
| 2904217 | 8/1980 | Fed. Rep. of Germany . | |
| 962585 | 7/1964 | United Kingdom | 252/548 |
| 1229134 | 4/1971 | United Kingdom | 252/548 |

*Primary Examiner*—Dennis Albrecht
*Attorney, Agent, or Firm*—Ernest G. Szoke; Henry E. Millson, Jr.; Mark A. Greenfield

[57] ABSTRACT

A microbially self-decontaminating dermatological cleansing concentrate containing at least one washing-active surfactant and at least one standard cleansing concentrate additive, and having a viscosity of about 500 to 5,000 mPas, improved by incorporating hydrogen peroxide, at least one fatty acid alkanolamide, and at least one water soluble alkali salt or ammonium salt; and a method for its use.

16 Claims, No Drawings

SELF-DECONTAMINATING CLEANSING PREPARATIONS

BACKGROUND OF THE INVENTION

1. Field of the Invention

This invention relates to cleansing preparations, especially hand cleansers, which self-decontaminate through the inclusion of hydrogen peroxide, but which nevertheless retain desired viscosities through the further inclusion of fatty acid alkanolamides and water-soluble alkali and/or ammonium salts.

2. Statement of Related Art

Water-miscible concentrates having a high surfactant content, for example of the handwashing lotion type, are ideal nutrient media for microorganisms, so that these products have to be protected against attack and decomposition by microorganisms, particularly bacteria, fungi and spore formers. The undesirable introduction of microorganisms such as these can occur, for example, during the preparation or during the use of the products. It is standard practice to protect cleansing preparations (or rather corresponding concentrates of the type in question) by means of preservatives, of which only a limited number are permitted under cosmetics legislation in many countries.

In most places, handwashing lotions are not subject to legislation or medicaments, although they have to satisfy praticular requirements in practice, particularly in the medical field, i.e. in hospitals, in general practice or, generally, in patient care. In the particular applications in question here, the water-miscible lotions are in greater danger of contamination by pathogenic microorganisms and spore formers. Accordingly, the corresponding cleansing preparations have to be able to eliminate any contamination occuring on their own. This is not possible with conventional preservatives which, in the permitted in-use concentrations, show only microbistatic activity and no microbicidal activity.

In order, therefore, to develop autosterile cleansing preparations of the handwashing lotion type, for the medical field, possibilities must be sought for achieving microbicidal activity by addition of small quantities of toxicologically and, in particular, dermatologically safe compounds in addition to the stabilization already achieved by the addition of preservatives.

It is known that self-decontaminating skin disinfectants can be obtained by addition of small quantities of hydrogen peroxide to aqueous disinfectants. Thus, published German patent application No. 29 04 217 describes disinfectants based on aqueous alcohol solutions additionally containing small quantities of hydrogen peroxide. Disinfectants of this type are capable of destroying involuntarily introduced spores and, thus, of keeping the disinfectant germ-free in use.

In order to improve the heptics (tactile qualities) and the handling of cleansing preparations of the type described above and, more particularly, handwashing lotions, it is standard practice to adjust them by means of organic thickeners to viscosities in the range of from 500 to 5,000 mPas and, more particularly to viscosities of from about 500 to 4,000 mPas, as measured with a Brookfield LVF rotational viscosimeter at 20° C., spindle 4/20 r.p.m. The addition of hydrogen peroxide to thickened surfactant-containing cleansing concentrates such as these seriously complicates their formulation, because the viscosity-regulating properties of conventional thickeners are lost by the addition of even small quantities of hydrogen peroxide.

DESCRIPTION OF THE INVENTION

Other than in the operating examples, or where otherwise indicated, all numbers expressing quantities of ingredients or reaction conditions used herein are to be understood as modified in all instances by the term "about".

The present invention provides surfactant-containing thickened cleansing preparations and, more particularly cleansing concentrates which, through the use of small quantities of hydrogen peroxide, are capable of autosterilization, but which nevertheless correspond to their physical properties to the desired viscous compositions.

To achieve this, the present invention sets out from the observation that the common use of hydrogen peroxide with the combination of fatty acid alkanolamides and water soluble salts described hereinafter leads to the desired property spectrum.

Accordingly, the present invention relates to thickened, water-miscible and autosterile detergent concentrates, more particularly for use as handwashing lotions in the medical field, which contain washing-active surfactants in addition to toxicologically and, in particular, dermatologically safe disinfectants and/or preservatives and which are characterized in that they contain, together with a small quantity of hydrogen peroxide, a combination of fatty acid alkanolamides and water-soluble alkali and/or ammonium salts as thickener.

According to the invention, this novel possiblity of viscosity regulation enables the viscosities of the washing lotions containing hydrogen peroxide to be adjusted to values in the range of particular relevance in practice, i.e. about 500 up to about 5,000 mPas and, more especially, in the range from about 500 to 4,000 mPas (Brookfield, determined as described above.)

The fatty acid alkanolamides are derived in particular from $C_{10-22}$, preferably $C_{12-18}$-fatty acids and are present in 0.2–5%, preferably 0.5–3.5%, by weight, based on the total weight of the formulation. The fatty acids may be saturated or partially olefinically unsaturated. Fatty acid alkanolamide mixtures derived from coconut oil fatty acids and from oleic acid are particularly suitable.

According to the invention, fatty acid dialkanolamides and, in particular, fatty acid diethanolamides are the preferred mixture components for viscosity regulation. Combinations of coconut oil fatty acid diethanolamide and oleic acid diethanolamide in weight ratios of 0.2–5:1 are particularly suitable.

Water-soluble alkali and/or ammonium salts are used together with the fatty acid alkanolamides. Non-corrosive, oxidation-stable simple salts of this type are preferred, particular significance being attributed to ammonium salts and more especially to ammonium sulfate.

Other suitable water-soluble salts include sodium and/or potassium salts of inorganic acids, such as sodium chloride, potassium chloride, sodium sulfate, as well as the corresponding salts of organic acids, such as potassium citrate. The salts should be present in 0.5–3%, preferably 0.8–2.5%, by weight based on the total weight of the formulation.

The cleansing concentrates normally contain the hydrogen peroxide in quantities which are microbially self-decontaminating effective, preferably or from 0.05 to at most 2% by weight, more preferably in quantities of from 0.1 to 1.5% by weight and most preferably in quantities of 0.2 to 1% by weight, based on the total weight of the cleansing concentrate. At least one standard cosmetic preservative as defined in Appendix VI of the European Community guidelines on cosmetics may optionally be present in a minimally preservative-effective amount, together with the hydrogen peroxide. Examples of preservatives such as these are: esters of p-hydroxybenzoic acid such as methyl or ethyl; bromo-5-nitro-1,3-dioxane; 2,2,4'-trichloro-2-hydroxydiphenylether; chlorhexidine; phenol derivatives; and aldehydes.

Where hydrogen peroxide and preservatives are used together, the weight ratio in which these non-$H_2O_2$ preservatives are mixed with the hydrogen peroxide is preferably in the range from 0 to 2:1.

Suitable surfactant components are any of the usual, relevant compounds, such as the known alkylether sulfates, amide ether sulfates, sulfosuccinic acid esters, protein-fatty acid condensates in the form of their Na or ($NH_4$) or ethanolamine salts.

In addition to the components mentioned thus far, the cleansing concentrates may contain other standard ingredients, such as reoiling agents, for example glycerol-E.O.-fatty acid esters, fatty alcoholpolyalkylene ethers, polyol-fatty acid esters, wax esters, pearlizers, for example fatty acid monoethanolamide, fatty alcohol ether sulfates, perfumes and/or dyes.

Particularly suitable cleansing concentrates of the type according to the invention contain the following components in the following quantities (percentages by weight, based on the total weight of the cleansing concentrate) in aqueous and/or water-soluble organic solution or suspension:

from 5 to 15% by weight of washing-active surfactants;
from 0.5 to 5% by weight of the other additives, such as reoiling agents, pearlizers, perfumes and/or dyes;
from 0.2 to 1% by weight of hydrogen peroxide, if desired in admixture with standard preservatives and/or disinfectants;
from 0.5 to 3.5% by weight of the fatty acid alkanolamides, more especially a combination of coconut oil fatty acid diethanolamide and oleic acid diethanolamide in a ratio of 0.2–5:1; and
from 0.8 to 2.5% of the alkali and/or ammonium salts;
with water q.s. to 100% by weight.

The viscosity of the cleansing concentrates is preferably adjusted to a value in the range of from 500 to 5,000 mPas and more especially to a value in the range of from 500 to 4,000 mPas. Concentrates of the type in question are self-decontaminating. In storage tests under varying climatic conditions, they are stable at temperatures in the range of from 0° to 40° C.

EXAMPLE

A handwashing lotion (lotion A) was prepared from the following components:

6% by weight sodium salt of a $C_{14}$-fatty alcohol ether sulfate+4 E.O.
3% by weight commercial triethanolamine salt of a condensate of protein hydrolyzate and fatty acid ("Lamepon" ST 40, a product of Chemische Fabrik Grunau, Illertissen, F.R. Germany)
1% by weight $C_{16}$ fatty acid monoethanolamide
2% by weight adduct of 8 E.O. with glycerol esterified with 3 mols coconut oil fatty acid
1% by weight propylene glycol
2% by weight ammonium sulfate
1% by weight coconut oil fatty acid diethanolamine 1% by weight oleic acid diethanolamide
0.2% by weight p-hydroxybenzoic acid methylester
0.2% by weight hydrogen peroxide q.s. to 100% by weight perfumes, dyes, water.

For comparison purposes, a handwashing lotion was prepared from the same components apart from the 0.2% by weight of hydrogen peroxide (Lotion B).

Samples of these lotions were massively contaminated with the germs listed in the following table and the lotions were observed for their microbiological behavior in storage.

| | Evaluation Results: | |
|---|---|---|
| Contamination with | Lotion A containing PHB-ester | Lotion B containing PHB-ester: $H_2O_2$ ratio of 1:1 |
| $4 \times 10^7$ CFU/ml of a mixture of *aspergillus* species, *penicillium* species, *candida* species, *pseudomonads*, *agromobacter* | still contains $4 \times 10^3$ CFU/0.1 ml after1 week | contains $1 \times 10^1$ CFU/0.1 ml after 24 hours germ-free after 48 hours |
| $1 \times 10^6$ CFU/ml hospital-specific mixture of *Pseudomonas aeruginosa*, *Pseudomonas cepacia* and other pathogenic germs | still contains germs after 1 week | germ-free after 24 hours |
| $1 \times 10^5$ CFU/100 ml spores of *Baccillus cerius* | spore content still high after 5 days | spore-free after less than 5 days |

CFU = colony-forming units

It is thus possible to prepare self-decontaminating handwashing lotions which are viscosity-stable after bacterial, fungal or spore contamination.

We claim:

1. In a water-miscible dermatological cleansing concentrate consisting essentially of about 5 to 15 wt% of at least one washing-active surfactant which is an alkylether sulfate, an amide ether sulfate, a sulfosuccinic acid ester, or a protein-fatty acid condensate, in the form of their Na or $NH_4$ salts; about 0.5 to 5 wt% of at least one standard cleansing concentrate additive; and having a viscosity of about 500 to 5,000 mPas,
the improvement of rendering said cleansing concentrate microbially self-decontaminating while maintaining its viscosity and water miscibility by incorporating therein ingredients consisting of:
(A) about 0.05 to 2 wt% of hydrogen peroxide;
(B) about 0.2 to 5 wt% of a fatty acid alkanolamide which is a combination of coconut oil fatty acid diethanolamide and oleic acid diethanolamide in a weight ratio of about 0.2–5:1;
(C) about 0.5 to 3 wt% of at least one water-soluble salt, which is ammonium sulfate; sodium chloride, potassium chloride, sodium sulfate, or potassium citrate; and
(D) at least one standard cosmetic preservative, either not present or present in at least a minimally preservative-effective amount, all wt% being based upon the total formulation weight, and wherein said viscosity is maintained after incorporating all of the above ingredients.

2. The concentrate of claim 1 wherein
(A) is present in about 0.1 to 1.5 wt%;

(B) is present in about 0.5 to 3.5 wt%; and (C) is present in about 0.8 to 2.5 wt%.

3. The concentrate of claim 2 wherein (B) is present in about 2 wt%.

4. The concentrate of claim 2 wherein (C) is present in about 2 wt%.

5. The concentrate of claim 2 wherein (D) is present in up to about 2 times the amount of (A), by weight.

6. The concentate of claim 1 wherein (A) is present in about 0.2 to 1 wt%.

7. The concentrate of claim 1 wherein (b) is present in about 2 wt%.

8. The concentrate of claim 1 wherein (C) is present in about 2 wt%.

9. The concentrate of claim 1 wherein (B) is a combination of coconut oil fatty acid diethanolamide and oleic acid ethanolamide, each present in about 1 wt%.

10. The concentrate of claim 1 wherein (B) and (C) together comprise up to about 4 wt%.

11. The concentrate of claim 1 wherein (D) is present in up to about 2 times the amount of (A), by weight.

12. The concentrate of claim 1 having an initial viscosity of about 500 to 4,000 mPas.

13. A method for cleansing hands comprising applying thereto the concentrate of claim 1 in a cleansing-effective amount, and rinsing the hands with water.

14. A method for cleansing hands comprising applying thereto the concentrate of claim 2 in a cleansing-effective amount, and rinsing the hands with water.

15. A method for cleansing hands comprising applying thereto the concentrate of claim 7 in a cleansing-effective amount, and rinsing the hands with water.

16. A method for cleansing hands comprising applying thereto concentrate of claim 10 in a cleansing-effective amount, and rinsing the hands with water.

* * * * *